US010035741B2

United States Patent
Horn et al.

(10) Patent No.: US 10,035,741 B2
(45) Date of Patent: Jul. 31, 2018

(54) HIGH THROUGHPUT OXIDATIVE DEHYDROGENATION PROCESS

(71) Applicant: TPC Group, Houston, TX (US)

(72) Inventors: Jillian M. Horn, Decatur, GA (US); Joseph G. Duff, League City, TX (US); Clifford A. Maat, Pearland, TX (US); Robert P. Adams, Missouri City, TX (US); John J. Senetar, Naperville, IL (US)

(73) Assignee: TPC Group LLC, Houston, TX (US)

( * ) Notice: Subject to any disclaimer, the term of this patent is extended or adjusted under 35 U.S.C. 154(b) by 0 days.

(21) Appl. No.: 15/249,545

(22) Filed: Aug. 29, 2016

(65) Prior Publication Data

US 2016/0368840 A1    Dec. 22, 2016

Related U.S. Application Data

(63) Continuation-in-part of application No. 14/771,302, filed as application No. PCT/US2014/021523 on Mar. 7, 2014.

(Continued)

(51) Int. Cl.
*C07C 5/327*    (2006.01)
*C07C 2/26*    (2006.01)
(Continued)

(52) U.S. Cl.
CPC ............... *C07C 5/48* (2013.01); *C08F 36/06* (2013.01)

(58) Field of Classification Search
CPC ................................. C07C 5/327; C07C 2/26
(Continued)

(56) References Cited

U.S. PATENT DOCUMENTS 3,207,810 A    9/1965 Bajars
3,728,415 A    4/1973 Arganbright
(Continued)

FOREIGN PATENT DOCUMENTS

JP    2011148720 A    8/2011

OTHER PUBLICATIONS

Seyed Hamed Mahdaviani et al., "Selective ethylene dimerization toward 1-butene by a new highly efficient catalyst system and determination of its optimum operating conditions in a Buchi reactor", International Journal of Chemical Engineering and Applications, Oct. 2010, pp. 276-281, vol. 1, No. 3.
(Continued)

*Primary Examiner* — Thuan D Dang
(74) *Attorney, Agent, or Firm* — Michael W. Feriell

(57) ABSTRACT

A method of oxidatively dehydrogenating a n-butenes to butadiene includes oxidatively dehydrogenating dehydrogenation reactant in a first adiabatic, catalytic reaction zone to provide a first-stage effluent stream enriched in butadiene at a first-stage effluent temperature above the first-stage inlet temperature, cooling the first-stage effluent stream in a first heat transfer zone to a second-stage inlet temperature lower than said first-stage effluent temperature to provide a second gaseous feed stream comprising superheated steam, n-butene and butadiene, wherein the second stage inlet temperature is lower than said first stage effluent temperature and oxidatively dehydrogenating n-butene in the second stream to provide a product stream further enriched in butadiene at a second stage effluent temperature above said second-stage inlet temperature. The first reaction zone temperature rise and the second reaction zone temperature rise are at least 200° F. (111° C.) and the first heat transfer zone temperature reduction is at least 50% of the value of the first reaction zone temperature rise.

18 Claims, 3 Drawing Sheets

Related U.S. Application Data

(60) Provisional application No. 62/212,620, filed on Sep. 1, 2015, provisional application No. 61/774,309, filed on Mar. 7, 2013.

(51) Int. Cl.
*C07C 5/48* (2006.01)
*C08F 36/06* (2006.01)

(58) Field of Classification Search
USPC .............. 585/616, 621, 633, 510, 324, 329
See application file for complete search history.

(56) References Cited

U.S. PATENT DOCUMENTS

| | | | |
|---|---|---|---|
| 3,911,042 A | 10/1975 | Belov et al. | |
| 3,925,498 A | 12/1975 | Stadig | |
| 3,953,370 A | 4/1976 | Miklas | |
| 3,969,429 A | 7/1976 | Belov et al. | |
| 4,069,272 A | 1/1978 | Hutson, Jr. | |
| 4,083,844 A | 4/1978 | Gottschlich et al. | |
| 4,658,074 A | 4/1987 | Bajars et al. | |
| 4,737,535 A * | 4/1988 | Furukawa ............ | B60C 1/0016 524/113 |
| 5,162,595 A | 11/1992 | Wu | |
| 6,998,504 B1 | 2/2006 | Unverricht et al. | |
| 7,034,195 B2 | 4/2006 | Schindler et al. | |
| 7,488,857 B2 | 2/2009 | Johann et al. | |
| 8,088,962 B2 | 1/2012 | Klanner et al. | |
| 2011/0288308 A1 | 11/2011 | Grasset et al. | |

OTHER PUBLICATIONS

L. Marshall Welch et al., "Butadiene via oxidative dehydrogenation", Hydrocarbon Processing, Nov. 1978, pp. 131-136.

International Search Report (in corresponding PCT parent application, i.e., PCT/US2014/021523) dated Aug. 28, 2014.

Written Opinion (in corresponding PCT parent application, i.e., PCT/US2014/021523) dated Aug. 28, 2014.

* cited by examiner

HIGH THROUGHPUT OXIDATIVE DEHYDROGENATION PROCESS

CLAIM FOR PRIORITY

This application is based upon U.S. Provisional Application No. 62/212,620 of the same title, filed Sep. 1, 2015. This application is also a continuation in part of copending U.S. patent application Ser. No. 14/771,302 entitled "Multi-Stage Oxidative Dehydrogenation Process with Inter-Stage Cooling", filed Aug. 28, 2015. U.S. patent application Ser. No. 14/771,302 was based on PCT Patent Application Serial No. PCT/US2014/021523, filed Mar. 7, 2014. PCT/US2014/021523 was based, in part, upon U.S. Provisional Application No. 61/774,309 filed Mar. 7, 2013, also entitled "Multi-Stage Oxidative Dehydrogenation Process with Inter-Stage Cooling". The priorities of the foregoing applications are hereby claimed and their disclosures incorporated herein by reference.

BACKGROUND

Oxidative dehydrogenation, particularly oxidative dehydrogenation of n-butenes to make 1,3 butadiene is known. Process details are discussed at some length in Welch et al., *Butadiene via oxidative dehydrogenation*, Hydrocarbon Processing, November 1978, pp. 131-136. A high ratio of superheated steam to hydrocarbon in the feed supplies the necessary heat and increases the per pass yields by reducing partial pressures. Steam also acts as a heat sink in an adiabatic reaction system to moderate temperature rise during the intensely exothermic reaction. U.S. Pat. No. 7,034,195, to Schindler et al., discusses a two stage oxydehydrogenation arrangement at Col. 10, lines 38-53, but does not address the temperature control. U.S. Pat. No. 8,088,962, to Klanner et al., mentions multi-zone reactors at Col. 17, lines 51-56 in connection with 2-zone multiple catalyst tube fixed bed reactors. See, also, U.S. Pat. No. 6,998,504, to Unverricht et al. which recites tube-bundle reactors.

U.S. Pat. No. 3,925,498 to Stadig discloses an oxidative dehydrogenation process wherein steam and oxygen are added in stages through spargers to increase oxygen levels and conversion of raw material.

Fixed bed, adiabatic reactors are preferred over tube-bundle reactors because of their simple construction, low capital costs and low operating and maintenance costs as well as well established operational know-how with these reactors. In a traditional version of the oxidative dehydrogenation process, a large flow of steam is used to control the exotherm.

SUMMARY OF INVENTION

It has been found in accordance with the invention that productivity, energy costs and raw material yields can be substantially improved by aggressive inter-stage cooling in a multi-stage oxidative dehydrogenation process. There is thus provided in accordance with the present invention a method of oxidatively dehydrogenating a dehydrogenation reactant in a multistage system including at least a first and second reaction zone and a heat transfer zone therebetween, wherein a first reaction zone temperature rise and a second reaction zone temperature rise are at least 200° F. (111° C.) and the heat transfer zone temperature reduction is at least 50% of the value of the first reaction zone temperature rise.

Among the unexpected, superior results seen are: (i)) increased conversion and selectivities; (ii) reduced steam costs; (iii) higher LHSV in the system; and (iv) extended catalyst life. Energy savings of 30% or more are readily achieved as compared with a conventional process. General, typical and preferred operating parameters for a three component system, including a first stage reactor, an inter-stage heat exchanger and a second stage reactor are provided in Tables 1, 2 and 3, as well as in Tables 4 and 6 presented hereinafter. In another aspect of the invention, butadiene produced in a multi-stage oxidative dehydrogenation process with aggressive inter-stage cooling is incorporated into polymeric products by polymerization with itself and/or with comonomers and/or intermediates. The polymeric materials so produced are subsequently incorporated into shaped articles.

BRIEF DESCRIPTION OF DRAWINGS

The invention is described in detail below with reference to the drawings wherein like numerals designate similar parts and wherein.

DETAILED DESCRIPTION

Figure 1:
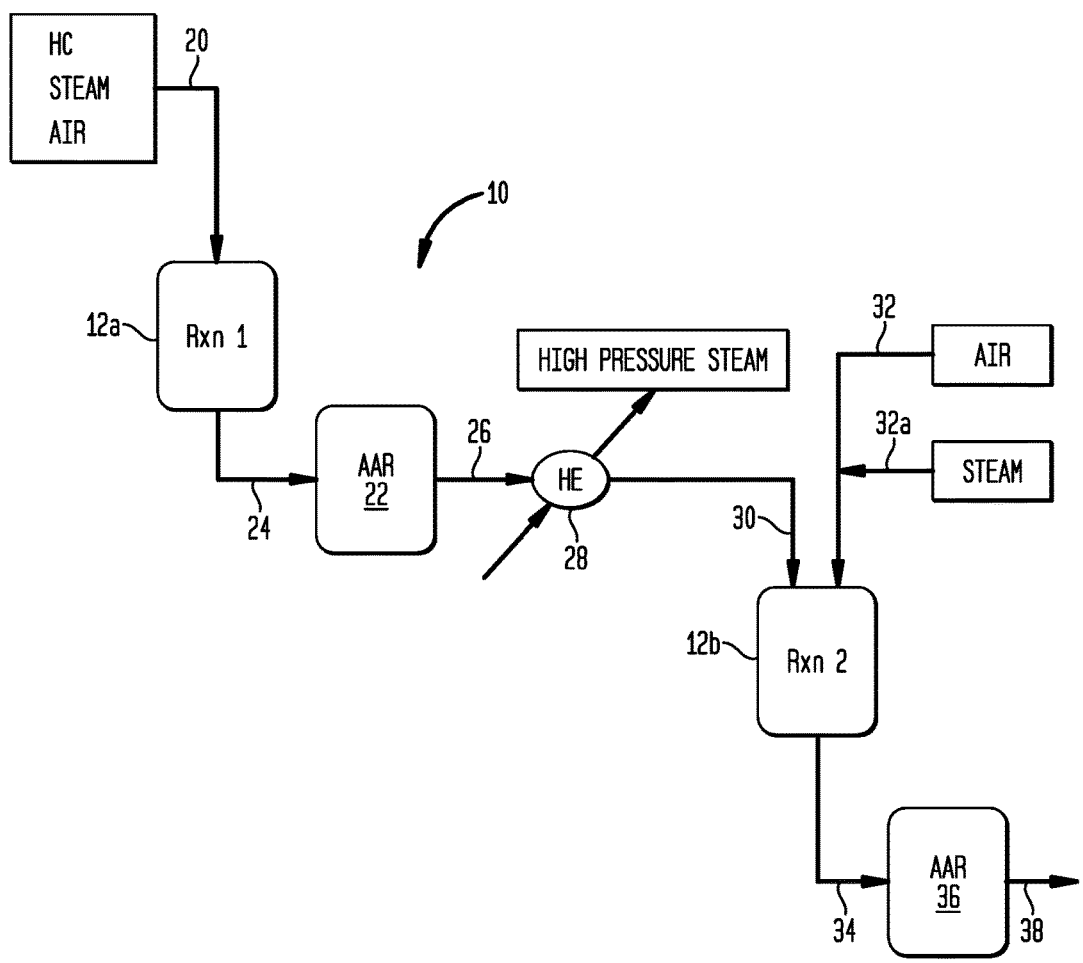
FIG. 1 is a schematic diagram illustrating a multi-stage reactor section with inter-stage cooling which is used to practice oxidative dehydrogenation in accordance with the invention.

The invention is described in detail below in connection with the Figures for purposes of illustration, only. The invention is defined in the appended claims. Terminology used throughout the specification and claims herein is given its ordinary meaning as supplemented by the discussion immediately below.

In general, the process of this invention can be applied to the dehydrogenation of a wide variety of organic compounds suitable as dehydrogenation reactants. Such compounds normally will contain from 2 to 20 carbon atoms, at least one

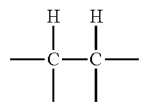

grouping, a boiling point below about 350° C., and may contain other elements, in addition to carbon and hydrogen, such as oxygen, halogens, nitrogen and sulfur. Preferred are compounds having 2 to 12 carbon atoms, and especially preferred, are compounds of 3 to 8 carbon atoms. Hydrocarbons of the above described carbon content form a preferred group.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, alkenes, and the like. Illustration of dehydrogenation includes propionitrile to acrylonitrile; propionaldehyde to acrolein; ethyl chloride to vinyl chloride; methyl isobutyrate to methyl methacrylate; 2 or 3 chlorobutane-1 or 2,3-dichlorobutane to chloroprene; ethyl pyridine to vinyl pyridine; ethylbenzene to styrene; isopropylbenzene to alpha-methyl styrene; ethylchlorohexane to styrene; to styrene; cyclohexane to benzene; methylbutene to isoprene; cyclopentane to cyclopentene and cyclopentadiene-1,3; n-octane to ethyl benzene and ortho-xylene; monomethylheptanes to xylenes; ethyl acetate to vinyl acetate; 2,4,4-trimethylpentene to xylenes; and the like.

More typically, the invention is applied to the manufacture of butadiene by way of oxidatively dehydrogenating n-butenes.

Unless otherwise indicated, "butadiene" or "BD" refers to 1,3 butadiene or mixtures comprising 1,3 butadiene. Feedstocks include butene-1 as well as cis and trans 2-butene.

"Conversion", "selectivity" and yield are related by the mathematical definition X(conversion)*S(selectivity)=Y (yield), all calculated on a molar basis unless otherwise indicated. For example, if 90% of substance A is converted (consumed), but only 80% of it is converted to the desired substance B and 20% to undesired by-products, so conversion of A is 90%, selectivity for B 80% and yield of substance B is 72% (=90%*80%). Specific values for conversions, selectivities and yields herein refer to the production of butadiene from n-butenes. Conversion and yields are per-pass (per 2-stage pass in the examples which follow).

Liquid hourly space velocity ("LHSV") based solely on the dehydrogenation reactant feed and is calculated as the hourly volumetric flow rate of liquid dehydrogenation reactant to the system divided by the volume of dehydrogenation catalyst beds in the multistage system. For purposes of Calculation of LHSV, the liquid density at atmospheric pressure and the boiling point of the reactant is used. A density of 0.6 g/ml is used for butene feed.

%, percent and like terminology means mole percent unless otherwise specifically indicated.

"Shaped article" refers to a three dimensional article such as a tire, a tube, a gasket or a housing, connectors, or other shaped product including: bellows in general; bladders; elastomeric closures, reservoirs; protective sleeves and coverings; dispensers; flanges; soft touch grips for instruments such as surgical instrument handles for tactile feel especially effective in wet environments to enhance grip (non-slip); trays; casings; valves; filters; stretch type hose with annular or spiral convolutions; accordion bellows used for protection for items such as screws; hydraulic and pneumatic seals; o-rings; belts; splash guards; and bumpers and components, therefor.

An oxidative dehydrogenation process for making butadiene of this invention (or other dehydrogenated product) includes providing a butene rich hydrocarbonaceous feed, vaporizing and superheating said hydrocarbonaceous butene rich feed, mixing said hydrocarbonaceous butene rich feed with superheated steam and an oxygen rich gas to form a reactor feed stream, hydrocarbonaceous butene rich feed and employing a reaction section with multiple reaction zones or stages and inter-stage cooling. Typically, a feed stream enters an adiabatic reaction zone at a temperature of 600-800° F. (315-427° C.) or so and exits that reaction zone at 1000-1150° F. (538-621° C.) or so. General parameters as to feed compositions and operating temperatures appear in Welch et al., *Butadiene via oxidative dehydrogenation*, Hydrocarbon Processing, noted above. Suitable oxidative dehydrogenation catalysts are also described in Miklas, METHOD OF ACTIVATING ZINC-FERRITE OXIDATIVE DEHYDROGENATION CATALYST; U.S. Pat. No. 3,953,370; Apr. 27, 1976, as well as CATALYTIC OXIDATIVE DEHYDROGENATION PROCESS; U.S. Pat. No. 4,658,074, and U.S. Pat. No. 4,083,844 to Purdy, the disclosures of which are incorporated herein by reference. Acetylene removal catalysts (AAR catalysts) and their usage are described in Application No. PCT/US2011/000624, the disclosure of which is also incorporated by reference.

The present invention may be practiced employing a variety of features as are disclosed in WO 2013/148913 entitled IMPROVED CONTROLLABILITY OXIDATIVE DEHYDROGENATION PROCESS FOR PRODUCING BUTADIENE, as well as WO 2014/138520 entitled MULTI-STAGE OXIDATIVE DEHYDROGENATION PROCESS WITH INTER-STAGE COOLING, the disclosures of which are incorporated herein by reference.

The method and apparatus of this invention is appreciated with reference to FIG. 1, which is a schematic diagram of a reaction section 10 that can be used in connection with the other equipment. In FIG. 1 hydrocarbon reactant is fed to a first adiabatic reactor along with steam via inlet 20 and less than a stoichiometric amount of oxygen, suitably ½ or so of a stoichiometric amount (i.e., 0.5 moles of oxygen for each mole of n-butene). In the first reactor 12a, a dehydrogenated product is produced by oxidative dehydrogenation and a temperature rise occurs. The effluent from reactor 12a is optionally fed (without cooling) to a separate vessel 22 containing a fixed bed of acetylene and aldehyde removal catalyst (AAR line 24). The high temperature of the effluent is desirable in order to facilitate impurity removal by the catalyst. Suitable AAR catalysts and their usage are described in Application No. PCT/US2011/000624 noted above. After treatment in the first AAR zone 22, the effluent is passed via line 26 to a heat exchanger 28 to produce superheated steam, which can be used in the process. The cooled effluent, which contains superheated steam, unreacted hydrocarbon reactant, and dehydrogenated product is fed via line 30 to a second reactor 12b along with the balance of a stoichiometric amount of oxygen via line 32 to complete the reaction. Additional steam is added via line 32a. The effluent from the second reactor is optionally fed via line 34 (again, without cooling) to another vessel 36 containing a fixed bed of acetylene and aldehyde removal catalyst. A product stream 38 exiting the system can be processed by conventional means to recover and purify the product.

When feeding air or oxygen to a reaction zone, it is preferable to mix in steam or inerts in order to avoid the flammable regions of the reaction mixture as discussed hereinafter. To this end, steam or other inerts are mixed with oxygen or the oxygen source employed prior to injection into the reactor at one or all oxygen injection points.

Figure 2:
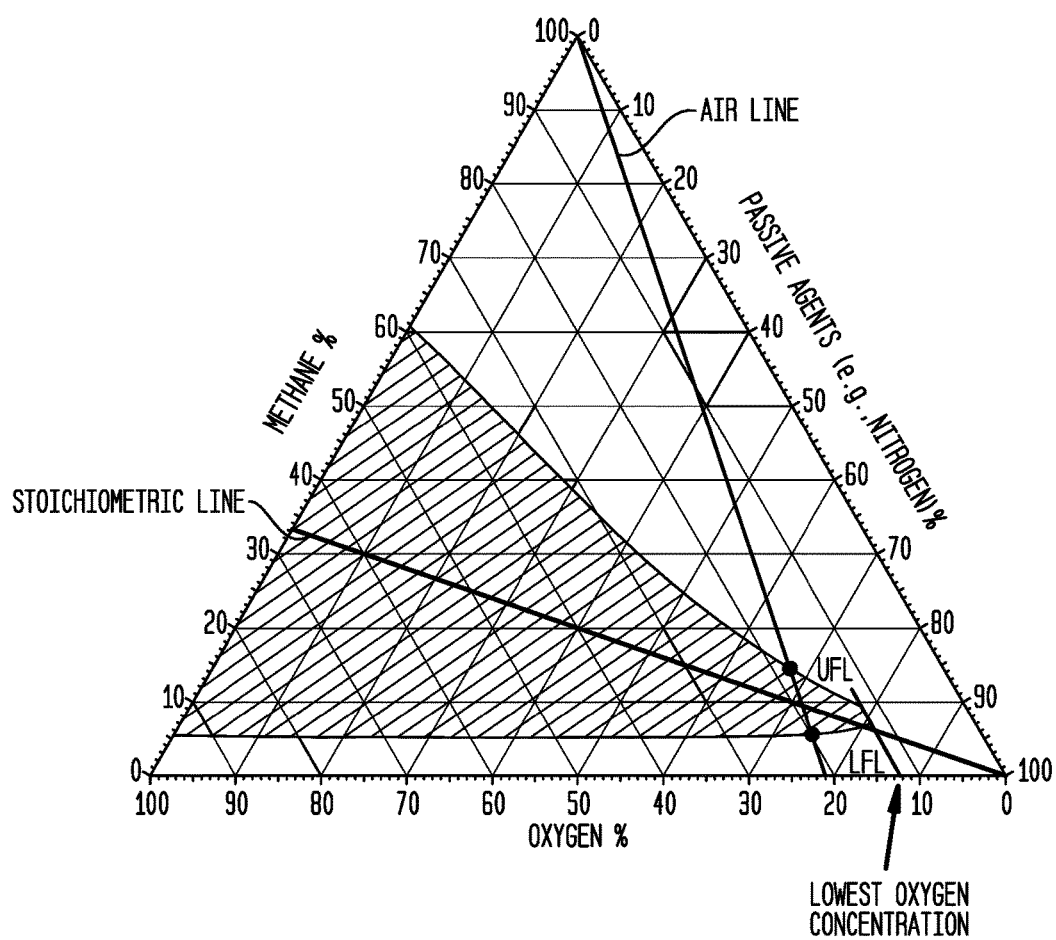
FIG. 2 is a ternary flammability diagram for methane/oxygen/inert gas mixtures sourced from http://cfbt-us.com/wordpress/?p=421. (2013 Attributed to GexCon)

Referring to FIG. 2, there is shown a ternary diagram illustrating the flammability region (shaded) of mixtures of methane/oxygen/and inerts such as nitrogen or steam on a mol % basis for a predetermined temperature and pressure. One of skill in the art will appreciate that the flammability region will vary depending on temperature, pressure, and composition of flammables/hydrocarbons in the reactor. It is seen in the diagram that at low levels of inerts especially, the flammability region for hydrocarbons is much expanded, as toward the left of the diagram. In operating the process of the present invention, it is much preferred to control the mixture composition, temperatures and pressures to operate outside of the flammability region of the reaction mixtures. A preferred method of operation is to add the oxygen to the steam and then mix the hydrocarbons. This avoids the "nose" of the flammability triangle and stays on the "fuel rich" side of the envelope.

For particular reaction compositions and conditions, flammability limits can be determined empirically or calculated from component data based on Le Chatelier's mixing rule, for example, for the lower flammability limit, LFL:

$$LFL_{Mix} = \frac{100}{\frac{C_1}{LFL_1} + \frac{C_2}{LFL_2} + \ldots + \frac{C_i}{LFL_i}}$$

Figure 3:
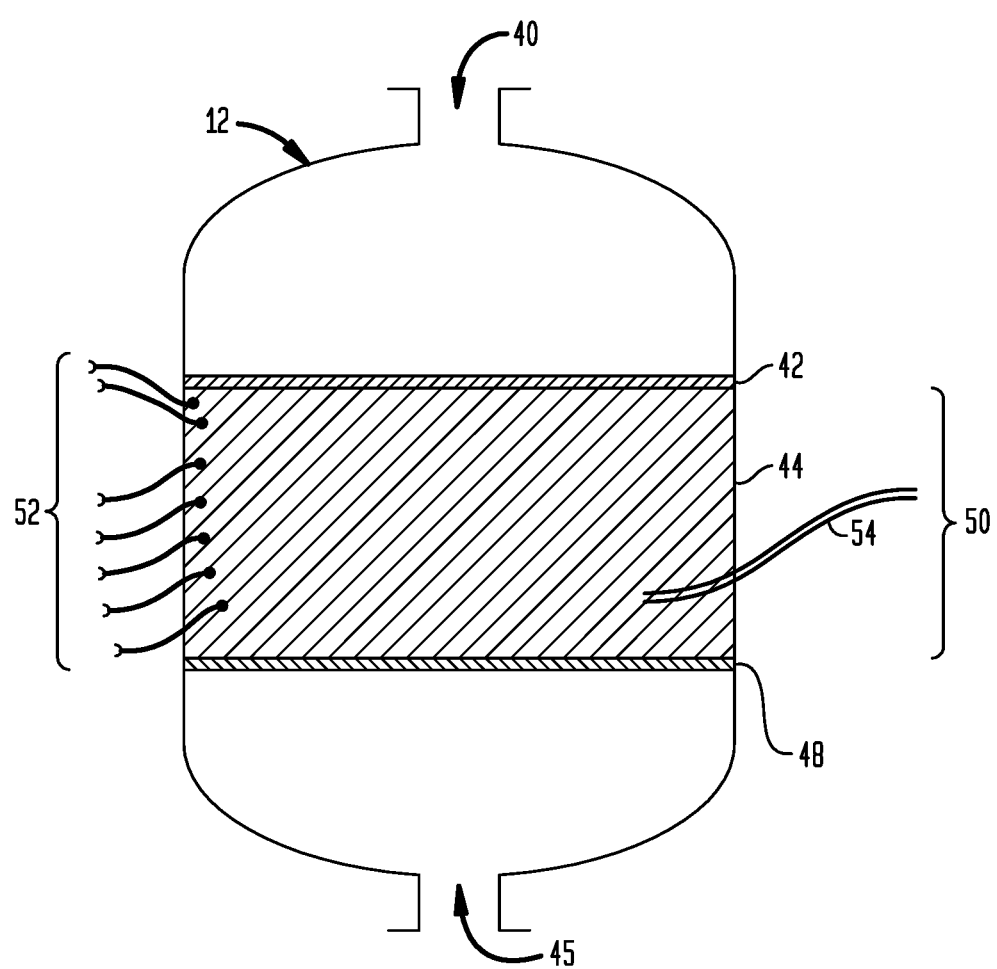
FIG. 3 is a schematic sectional view of a reactor for use in the practice of the present invention.

Referring to FIG. 3, there is shown a reactor 12 which can be used as either or both reactors 12a, 12b in FIG. 1. Hydrocarbon or other reactant enters reactor 12 through an upper inlet port 40 of reactor 12 and flows downwardly before impacting upon layer 42 of inert granules of refractory material such as alumina. The refractory material may be graded spheres. Upper layer 42 may be from about 50 mm to about 100 mm in depth, such as from about 65 to 85 mm in depth and in some cases from about 70 to 80 mm.

Oxidative dehydrogenation catalyst particles are disposed in layer or bed 44 having a depth of anywhere from 50-100 cm (20-40"). Butene rich hydrocarbonaceous feed is converted to a butadiene enriched reaction product stream which proceeds downstream of layer or bed 44 of oxidative dehydrogenation catalyst.

Beneath layer 44 there is provided inert support layer 48 comprised of refractory material graded spheres (small to large), with inert support layer 48 being preferably from about 2.54 cm (1") to about 20 cm (8") in depth, preferably from about 5.08 cm (2") to about 10 cm (4") in depth, more preferably from about 6.4 cm to 8.9 cm (2.5 to 3.5") in depth and even more preferably from about 6.99 cm to 7.62 cm (2.75 to 3"). The three layers, 42, 44, 48 make up a fixed bed 50 of the reactor.

After exiting inert support layer 48, the butadiene enriched product stream exits reactor 40 though the lower exit port 45 for subsequent recovery of the heat value contained therein and/or concentration of the butadiene content into a crude butadiene stream by way of purification as is noted above and as is further discussed in WO 2013/148913. The concentrated stream has a concentration of approximately 50 to 60% butadiene.

Typically, the catalytic process is initiated by raising the temperature of the catalyst bed to about 425° C. (800° F.); adding reactants until conversion is observed, then reducing the inlet temperatures to control the catalyst bed temperature. In most cases, natural gas is used to bring the streams up to temperature; then use of natural gas is sharply curtailed or cut off entirely once conversion is observed. In steady operation, as butene-rich feed initially impacts upon the catalyst bed, the inlet conditions are carefully controlled so that most of the conversion of butenes into butadiene occurs in the last several cm of layer 44 of oxidative dehydrogenation catalyst, which initially registers as essentially a step change in temperature recorded by only the lowest of those thermocouples 52 distributed throughout layer 44 of oxidative dehydrogenation catalyst, the thermocouples in the layer of oxidative dehydrogenation catalyst wherein the reaction is occurring. As the reaction progresses, oxidative dehydrogenation catalyst in the lowermost portion of layer 44 of oxidative dehydrogenation catalyst becomes deactivated which is indicated by decline in the registered temperature and may be reflected in selectivity or yield measurements as well. When the lower thermocouples in the array begin to register a decline in temperature the inlet temperature is increased slightly to move the reaction zone upwardly in the oxidative dehydrogenation catalyst. In this way, coking of catalyst in layers of oxidative dehydrogenation catalyst above the layer in use is avoided. When the uppermost layer of oxidative dehydrogenation catalyst becomes deactivated to the extent that catalyst changeout is called for, the process is interrupted and a new catalyst bed is supplied.

The location of the intensely exothermic reaction occurring in each reactor is monitored through a number of remotely readable thermocouples 52 spaced along the height of oxidation-dehydrogenation layer 44 so that the location of the reaction zone therein may be determined. The amount of oxygen remaining in the product stream is monitored with oxygen analyzer 54 located near the bottom of layer 44 so that oxygen breakthrough is avoided.

In order to control the system, a target temperature for a reaction zone is pre-selected and maintained in the reaction zone. The active regions in layer 44 are initially disposed near the bottom of layer 44. The reaction region or "active" region of oxydehydrogenation catalyst layer 44 is characterized by a relatively sharp rise in temperature over a relatively short bed depth to the pre-selected target temperature. Generally, the reaction zone is characterized by a temperature rise of from 100° F. to 300° F. (55° C. to 167° C.) over a bed depth change of from 1 to 5 inches (2.5 cm to 13 cm) to the target temperature. More typically, the active layer is characterized by a temperature rise of from 150° F. to 250° F. (83° C. to 139° C.) over a bed depth of from 2 to 4 inches (5 cm to 10 cm). Below the reaction zone in bed 44, there is preferably no additional temperature rise if the system is controlled properly since oxygen is completely or nearly completely depleted in the reaction zone and is no longer present in the system.

Suitable operating target temperatures for the oxydehydrogenation active region are from 1000° F. to 1200° F. (540° C. to 650° C.). When the targeted temperature of the reaction zone begins to fall, the inlet temperature to the reactor is raised and the active zone migrates upwardly in layer 44. One can estimate the time for oxygen breakthrough based on the rate of change of temperatures in the bed which is manifested in the rate of upward migration of the reaction zone and the remaining bed depth above the reaction zone. The estimate of time to breakthrough is based on the temperature readings in the layers above the reaction zone (which are lower than the target temperature for the reaction zone) more so than on the temperatures at or below the reaction zone since the temperatures above the reaction zone are indicative of relatively fresh catalyst available to catalyze the reaction. Thus, if the temporal temperature profile indicates that the reaction zone is migrating upwardly at a rate of 0.5 cm/day and the uppermost thermocouple(s) indicate a fresh catalyst layer of 5 cm, only 10 days of operation remain before oxygen breakthrough, provided that the oxydehydrogentation catalyst exhaustion rate remains relatively constant.

By controlling migration of the reaction zone in the manner described herein, the oxidative dehydrogenation catalyst gives best performance for extended times.

General, typical and preferred operating parameters for a three component system, including a first stage reactor, an inter-stage heat exchanger and a second stage reactor are provided in Tables 1, 2, 3 and 4, below.

TABLE 1

First-Stage Reactor Operating Guidelines

| | General | Typical | Preferred |
|---|---|---|---|
| Oxygen/Reactant Molar Ratio | 0.15-0.8 | 0.2-0.7 | 0.35-0.55 |

TABLE 1-continued

First-Stage Reactor Operating Guidelines

|  | General | Typical | Preferred |
|---|---|---|---|
| First-Stage Steam/Reactant Molar Ratio | <10 | 6-9.5 | 7.5-9.5 |
| Temperature Delta (increase) from Inlet to Outlet ° F. (° C.) | 150-900 (83-500) | 250-600 (139-333) | 275-400 (97-222) |

TABLE 2

Heat Exchange Cooling Guidelines

|  | General | Typical | Preferred |
|---|---|---|---|
| Temperature Delta (decrease) from Heat Exchanger Inlet to Heat Exchanger Outlet ° F. (° C.) | 100-750 (56-417) | 200-600 (111-333) | 250-500 (138-278) |

TABLE 3

Second Stage Reactor and Overall Operating Guidelines

|  | General | Typical | Preferred |
|---|---|---|---|
| Total Oxygen/Reactant Molar Ratio | 0.5-1.25 | 0.7-1.1 | 0.8-1.05 |
| Second Stage Oxygen Added/Reactant Molar Ratio | 0.2-0.7 | 0.25-0.6 | 0.35-0.55 |
| Second Stage Added Steam/Reactant Molar Ratio | 0-10; 0.5-9; 2-8 | 3-8; 3-7 | 3.5-7; 4-6 |
| Total Steam/Reactant Molar Ratio with Added Steam in Stage 2 | 8-16 | 10-15 | 12-15 |
| Temperature Delta (increase) from Inlet to Outlet ° F. (° C.) | 150-900 (83-500) | 250-600 (139-333) | 275-400 (97-222) |
| LHSV (combined Stage 1 and Stage 2) hr$^{-1}$ | >3 | 3-4.5 | 3.5-4 |

TABLE 4

Temperature Guidelines for 2-Stage Butadiene Production

|  | General | Typical | Preferred |
|---|---|---|---|
| First Stage Inlet Temp ° F. (° C.) | 400-900 (205-480) | 500-850 (260-455) | 600-800 (315-425) |
| First Stage Outlet Temp ° F. (° C.) | 800-1250 (425-675) | 900-1200 (480-650) | 1000-1150 (540-620) |
| Heat Exchanger Inlet Temp ° F. (° C.) | 800-1250 (425-675) | 900-1200 (480-650) | 1000-1150 (540-620) |
| Heat Exchanger Outlet Temp ° F. (° C.) | 400-900 (205-480) | 500-850 (260-455) | 600-800 (315-425) |
| Second Stage Inlet Temp ° F. (° C.) | 400-900 (205-480) | 500-850 (260-455) | 600-800 (315-425) |
| Second Stage Outlet Temp ° F. (° C.) | 800-1250 (425-675) | 900-1200 (480-650) | 1000-1150 (540-620) |

EXAMPLES

Using the equipment and procedures described generally above, butene-1 was dehydrogenated in a two-stage system constructed generally in accordance with FIG. 1, equipped with two 25 cm (10") deep dehydrogenation catalyst beds and two 15 cm (6") AAR catalyst beds using aggressive inter-stage cooling. Results and details appear in Table 5 as Examples 1-6 wherein the system was operated with an LHSV of 3.6 hr$^{-1}$, a steam to butene ratio of 9 in the first stage and a steam to butene feed ratio of 14 in the second stage. Comparative Examples A, B and C were conducted under essentially the same conditions using a single stage reaction system with an LHSV of 2 hr$^{-1}$ and a steam to hydrocarbon ratio of approximately 14.

TABLE 5

Butene-1 Oxidative Dehydrogenation to Butadiene Results

| Run Number | $O_2$: Feed Butene-1 Stage 1 | $O_2$: Feed Butene-1 Stage 2 | Total $O_2$: Feed Butene-1 | Selectivity (mol %) | Conversion (mol %) | Yield (mol %) |
|---|---|---|---|---|---|---|
| 1 | 0.286 | 0.286 | 0.572 | 93.2% | 71.0% | 66.1% |
| 2 | 0.286 | 0.55 | 0.836 | 89.9% | 86.1% | 77.4% |
| 3 | 0.55 | 0.286 | 0.836 | 90.4% | 89.3% | 80.7% |
| 4 | 0.55 | 0.5 | 1.05 | 93.9% | 86.6% | 81.3% |
| 5 | 0.286 | 0.47 | 0.756 | 91.6% | 83.4% | 76.4% |
| 6 | 0.47 | 0.286 | 0.756 | 91.6% | 87.1% | 79.8% |
| A | 0.286 | NA | 0.286 | 93.1% | 38.9% | 36.3% |
| B | 0.55 | NA | 0.55 | 92.1% | 66.1% | 60.9% |
| C | 0.47 | NA | 0.47 | 92.7% | 59.4% | 55.1% |

It is appreciated from Table 5 that conversions and yields are much improved with the two-stage system of the invention as opposed to single stage reactor operation.

General and preferred operating protocols for the two-stage system is provided in Table 6 below for butadiene production from n-butene.

TABLE 6

Operating Protocol for Butadiene Production

| Feature | General Range(s) | Preferred Range(s) |
|---|---|---|
| LHSV hr$^{-1}$ | 3-10 | ≥3 up to 7.5 or 10; ≥3.5 up to 7 or 10 |
| Conversion (mol %) | 80-95 | ≥85; ≥90; ≥92 |
| Selectivity (mol %) | 90-95 | ≥90; ≥92 |
| Yield (mol %) | 65-95; 70-90 | 75-85; 77.5-85 |
| Hours of continuous operation | ≥2400 2400-9600 | ≥3600 ≥4200 |

Butadiene produced in accordance with the present invention is incorporated into polymeric products by polymerization with itself and/or with comonomers and/or intermediates. Suitable techniques for polymerizing butadiene are discussed in *Encyclopedia of Polymer Science and Technology*, "Butadiene Polymers", Vol. 5, pp. 317-356, Kearns, M., Wiley, 2002, as well as the references listed in this encyclopedia excerpt.

Typical polymeric products include acrylonitrile-butadiene-styrene (ABS) resins, styrene butadiene copolymer latexes, thermoplastic elastomers, Nylon® 66 (made with hexamethylene diamine derived from butadiene through adiponitrile) and the like, as well as a variety of butadiene rubber products such as emulsion styrene-butadiene rubber, solution styrene-butadiene rubber, polybutadiene rubber, nitrile rubber, and polychloroprene (Neoprene®) rubber.

Styrene-butadiene rubber and polybutadiene rubber are extensively used to manufacture tires.

There is thus provided in accordance with the present invention processes for producing oxidative dehydrogenation products and their use in polymeric compositions and the use of butadiene so made in butadiene rubber which may be subsequently incorporated into tires. Various preferred embodiments of the invention are enumerated below and in the attached claims.

Embodiment No. 1 is a method of oxidatively dehydrogenating a dehydrogenation reactant comprising:
(a) providing a first gaseous feed stream to a first adiabatic, catalytic reaction zone at a first-stage inlet temperature, the first feed stream including a dehydrogenation reactant, oxygen and superheated steam, wherein the molar ratio of superheated steam to dehydrogenation reactant is less than 10 mol/mol;
(b) oxidatively dehydrogenating dehydrogenation reactant in said first adiabatic, catalytic reaction zone to provide a first-stage effluent stream enriched in said dehydrogenated product at a first-stage effluent temperature above said first-stage inlet temperature, by an amount referred to as a first reaction zone temperature rise;
(c) cooling the first-stage effluent stream in a first heat transfer zone to a second-stage inlet temperature lower than said first-stage effluent temperature to provide a second gaseous feed stream comprising superheated steam, dehydrogenation reactant and dehydrogenated product, wherein the second stage inlet temperature is lower than said first stage effluent temperature by an amount referred to as a first heat transfer zone temperature reduction;
(d) feeding said second gaseous feed stream at said second-stage inlet temperature to a second adiabatic, catalytic reaction zone along with additional oxygen and additional stream, said additional steam being added in an amount of from 0 mol/mol to 10 mol/mol of steam/dehydrogenation reactant;
(e) oxidatively dehydrogenating dehydrogenation reactant in said second adiabatic, catalytic reaction zone to provide a second stage effluent stream further enriched in said dehydrogenated product at a second stage effluent temperature above said second-stage inlet temperature by an amount referred to as a second reaction zone temperature rise,
wherein said first reaction zone temperature rise and said second reaction zone temperature rise are at least 200° F. (111° C.) and said first heat transfer zone temperature reduction is at least 50% of the value of the first reaction zone temperature rise.

Embodiment No. 2 is the method according to Embodiment No. 1, wherein said first reaction zone temperature rise and said second reaction zone temperature rise are at least 250° F. (139° C.).

Embodiment No. 3 is the method according to Embodiment No. 1, wherein said first reaction zone temperature rise and said second reaction zone temperature rise are at least 350° F. (194° C.).

Embodiment No. 4 is the method according to Embodiment No. 1, wherein said first reaction zone temperature rise and said second reaction zone temperature rise are from 275° F. (153° C.) to 400° F. (222° C.).

Embodiment No. 5 is the method according to Embodiment No. 1, wherein the first reaction zone temperature rise or the second reaction zone temperature rise are from 275° F. (153° C.) to 400° F. (222° C.).

Embodiment No. 6 is the method according to Embodiment No. 1, wherein said first-stage effluent temperature and said second stage effluent temperature are less than 1200° F. (667° C.).

Embodiment No. 7 is the method according to Embodiment No. 1, wherein said first heat transfer zone temperature reduction is at least 75% of the value of the first reaction zone temperature rise.

Embodiment No. 8 is the method according to Embodiment No. 1, wherein said first heat transfer zone temperature reduction is at least 85% of the value of the first reaction zone temperature rise.

Embodiment No. 9 is the method according to Embodiment No. 1, wherein said first heat transfer zone temperature reduction is at least 90% of the value of the first reaction zone temperature rise.

Embodiment No. 10 is the method according to Embodiment No. 1, wherein the amount of steam added to the second gaseous feed stream is from 0.5 mol/mol to 9 mol/mol of steam/dehydrogenation reactant such that the total steam added is from 8 mol/mol to 16 mol/mol of steam/dehydrogenation reactant.

Embodiment No. 11 is the method according to Embodiment No. 1, wherein the amount of steam added to the second gaseous feed stream is from 3 mol/mol to 7 mol/mol of steam/dehydrogenation reactant such that the total steam added is from 8 mol/mol to 16 mol/mol of steam/dehydrogenation reactant.

Embodiment No. 12 is the method according to Embodiment No. 1, wherein the amount of steam added to the second gaseous feed stream is from 4 mol/mol to 6 mol/mol of steam/dehydrogenation reactant such that the total steam added is from 8 mol/mol to 16 mol/mol of steam/dehydrogenation reactant.

Embodiment No. 13 is the method according to Embodiment No. 1, wherein the ratio of steam to dehydrogenation reactant in said first gaseous feed stream is from 6 mol/mol to 9.5 mol/mol.

Embodiment No. 14 is the method according to Embodiment No. 13, wherein the amount of steam added to the second gaseous feed stream is from 0.5 mol/mol to 6.0 mol/mol of steam/dehydrogenation reactant such that the total steam added is from 8.5 mol/mol to 15 mol/mol of steam/dehydrogenation reactant.

Embodiment No. 15 is the method according to Embodiment No. 1, wherein the molar ratio of oxygen to dehydrogenation reactant in said first gaseous feed stream is from 0.2:1 to 0.7:1.

Embodiment No. 16 is the method according to Embodiment No. 1, wherein the molar ratio of oxygen to dehydrogenation reactant in said first gaseous feed stream is from 0.25:1 to 0.6:1.

Embodiment No. 17 is the method according to Embodiment No. 1, wherein the molar ratio of oxygen to dehydrogenation reactant in said first gaseous feed stream is from 0.35:1 to 0.55:1.

Embodiment No. 18 is the method according to Embodiment No. 17, wherein additional oxygen is added to said second gaseous feed stream such that the total oxygen feed to the first and second adiabatic reaction zones has a molar ratio of oxygen:dehydrogenation reactant of from 0.7:1 to 1.1:1.

Embodiment No. 19 is the method according to Embodiment No. 15, wherein the oxygen in the first gaseous feed stream is substantially consumed in the first adiabatic, catalytic reaction zone and additional oxygen is added to said second gaseous feed stream such that the total oxygen feed to the first and second adiabatic reaction zones has a molar ratio of oxygen:dehydrogenation reactant of from 0.5:1 to 1.1:1.

Embodiment No. 20 is the method according to Embodiment No. 16, wherein the oxygen in the first gaseous feed stream is substantially consumed in the first adiabatic, catalytic reaction zone and additional oxygen is added to said second gaseous feed stream such that feed to the second adiabatic reaction zone has a molar ratio of oxygen:dehydrogenation reactant of from 0.25:1 to 0.6:1.

Embodiment No. 21 is the method according to Embodiment No. 17, wherein the oxygen in the first gaseous feed stream is substantially consumed in the first adiabatic, catalytic reaction zone and additional oxygen is added to said second gaseous feed stream such that feed to the second adiabatic reaction zone has a molar ratio of oxygen:dehydrogenation reactant of from 0.35:1 to 0.55:1.

Embodiment No. 22 is the method according Embodiment No. 1, wherein said dehydrogenation reactant comprises butenes and said dehydrogenated product comprises butadiene.

Embodiment No. 23 is the method according to Embodiment No. 22, wherein the LHSV of the butenes is greater than 3.

Embodiment No. 24 is the method according to Embodiment No. 23, wherein the LHSV of the butenes is greater than 3.5.

Embodiment No. 25 is the method according to Embodiment No. 22, wherein the LHSV of the butenes is from 3 to 10.

Embodiment No. 26 is the method according to Embodiment No. 22, wherein the conversion of butenes is 85 mol % or greater.

Embodiment No. 27 is the method according to Embodiment No. 26, wherein the conversion of butenes is 90 mol % or greater.

Embodiment No. 28 is the method according to Embodiment No. 27, wherein the selectivity to butadiene is 92 mol % or greater.

Embodiment No. 29 is the method according to Embodiment No. 22, wherein the selectivity to butadiene is from 90 mol % to 95 mol %.

Embodiment No. 30 is the method according to Embodiment No. 22, wherein the yield of butadiene is from 70 mol % to 90 mol %.

Embodiment No. 31 is the method according to Embodiment No. 22, wherein the yield of butadiene is from 75 mol % to 85 mol %.

Embodiment No. 32. The method according to Embodiment No. 22, wherein the yield of butadiene is from 77.5 mol % to 85 mol %.

Embodiment No. 33 is the method according to Embodiment No. 1, wherein said step of cooling said first stage effluent stream comprises indirect heat transfer.

Embodiment No. 34 is the method according to Embodiment No. 1, wherein said step of cooling said first stage effluent stream comprises direct heat transfer utilizing a tube and shell heat exchanger or a plate and frame heat exchanger.

Embodiment No. 35 is the method according to Embodiment No. 1, further comprising contacting at least one of the reaction zone effluent streams with an acetylene removal catalyst.

Embodiment No. 36 is the method according to Embodiment No. 35, wherein the acetylene removal catalyst comprises Ni, Fe, an alkali metal, and optionally an alkaline earth element.

Embodiment No. 37 is the method according to Embodiment No. 1, wherein said first adiabatic catalytic reaction zone and said second adiabatic catalytic reaction zone are housed in separate vessels.

Embodiment No. 38 is the method according to Embodiment No. 37, wherein said first heat transfer zone is housed in a vessel separate from the vessels housing said first and second adiabatic catalytic reaction zones.

Embodiment No. 39 is a method of oxidatively dehydrogenating a dehydrogenation reactant comprising:
- (a) providing a first gaseous feed stream to an inlet of a first adiabatic, catalytic reaction zone comprising a first catalyst bed of granules of oxidative dehydrogenation catalyst at a first-stage inlet temperature, the first feed stream including a dehydrogenation reactant, oxygen and superheated steam, wherein the molar ratio of superheated steam to dehydrogenation reactant is less than 10 mol/mol,
- said first catalyst bed of oxidative dehydrogenation catalyst having associated therewith a plurality of temperature sensing devices adapted to measure temperature in the first catalyst bed along a direction of flow;
- (b) oxidatively dehydrogenating dehydrogenation reactant in said first adiabatic, catalytic reaction zone to provide a first-stage effluent stream enriched in said dehydrogenated product at a first-stage effluent temperature above said first-stage inlet temperature, by an amount referred to as a first reaction zone temperature rise,
- while controlling inlet conditions to said first adiabatic reaction zone such that the oxidative dehydrogenation reaction initially occurs in the layers of said first catalyst bed most distal to said inlet of said first reaction zone, including in an active region of the first catalyst bed of said first catalytic reaction zone and monitoring the temperature along the length of the bed and from time to time, increasing the inlet temperature so that the active region of the catalyst bed of said first catalytic reaction zone migrates toward said first reaction zone inlet;
- (c) cooling the first-stage effluent stream in a first heat transfer zone to a second-stage inlet temperature lower than said first-stage effluent temperature to provide a second gaseous feed stream comprising superheated steam, dehydrogenation reactant and dehydrogenated product, wherein the second stage inlet temperature is lower than said first stage effluent temperature by an amount referred to as a first heat transfer zone temperature reduction;
- (d) feeding said second gaseous feed stream at said second-stage inlet temperature to a second adiabatic, catalytic reaction zone comprising a second catalyst bed of granules of oxidative dehydrogenation catalyst along with additional oxygen and additional steam, said additional stream being added in an amount of from 0 mol/mol to 10 mol/mol of steam/dehydrogenation reactant,
- said second catalyst bed of oxidative dehydrogenation catalyst having associated therewith a plurality of temperature sensing devices adapted to measure temperature in the first catalyst bed along a direction of flow;
- (e) oxidatively dehydrogenating dehydrogenation reactant in said second adiabatic, catalytic reaction zone to provide a second stage effluent stream further enriched in said dehydrogenated product at a second stage effluent temperature above said second-stage inlet temperature by an amount referred to as a second reaction zone temperature rise,
while controlling inlet conditions to said second adiabatic reaction zone independently of controlling inlet conditions to said first adiabatic, catalytic reaction zone such that the oxidative dehydrogenation reaction initially occurs in the second adabiatic, catalytic reaction zone in the layers of said second catalyst bed most distal to said inlet of said second reaction zone, including in an active region of the second catalyst bed of said second catalytic reaction zone and monitoring the temperature along the length of the bed and from time to time, increasing the inlet temperature so that the active region of the catalyst bed of said second catalytic reaction zone migrates toward said second reaction zone inlet,
wherein said first reaction zone temperature rise and said second reaction zone temperature rise are at least 200° F. (111° C.) and said first heat transfer zone temperature reduction is at least 50% of the value of the first reaction zone temperature rise.

Embodiment No. 40 is the method of oxidatively dehydrogenating a dehydrogenation reactant according to Embodiment No. 39, wherein the temperature sensing devices comprise thermocouples.

Embodiment No. 41 is the method of oxidatively dehydrogenating a dehydrogenation reactant according to Embodiment No. 39, operated continuously for at least 2400 hours.

Embodiment No. 42 is the method of oxidatively dehydrogenating a dehydrogenation reactant according to Embodiment No. 41, operated continuously for at least 3600 hours.

Embodiment No. 43 is the method of oxidatively dehydrogenating a dehydrogenation reactant according to Embodiment No. 42, operated continuously for at least 4200 hours.

Embodiment No. 44 is the method of oxidatively dehydrogenating a dehydrogenation reactant according to Embodiment No. 41, operated continuously for at least 2400 hours and up to 9600 hours.

Embodiment No. 45 is a method of making a polymeric butadiene composition comprising:
(a) oxidatively dehydrogenating a linear butene by way of:
(i) providing a first gaseous feed stream to a first adiabatic, catalytic reaction zone at a first-stage inlet temperature, the first feed stream including said butene, oxygen and superheated steam, wherein the molar ratio of superheated steam to butene is less than 10 mol/mol;
(ii) oxidatively dehydrogenating butene in said first adiabatic, catalytic reaction zone to provide a first-stage effluent stream enriched in butadiene at a first-stage effluent temperature above said first-stage inlet temperature, by an amount referred to as a first reaction zone temperature rise;
(iii) cooling the first-stage effluent stream in a first heat transfer zone to a second-stage inlet temperature lower than said first-stage effluent temperature to provide a second gaseous feed stream comprising superheated steam, butene and butadiene, wherein the second stage inlet temperature is lower than said first stage effluent temperature by an amount referred to as a first heat transfer zone temperature reduction;
(iv) feeding said second gaseous feed stream at said second-stage inlet temperature to a second adiabatic, catalytic reaction zone along with additional oxygen and additional stream, said additional steam being added in an amount of from 0 mol/mol to 10 mol/mol of steam/butene;
(v) oxidatively dehydrogenating butene in said second adiabatic, catalytic reaction zone to provide a second stage effluent stream further enriched in butadiene at a second stage effluent temperature above said second-stage inlet temperature by an amount referred to as a second reaction zone temperature rise,
wherein said first reaction zone temperature rise and said second reaction zone temperature rise are at least 200° F. (111° C.) and said first heat transfer zone temperature reduction is at least 50% of the value of the first reaction zone temperature rise; and
(b) incorporating the butadiene so produced into the polymeric butadiene composition.

Embodiment No. 46 is the method of making a polymeric butadiene composition according to Embodiment No. 45, wherein the polymeric butadiene composition is selected from the group consisting of: acrylonitrile-butadiene-styrene resins; styrene butadiene copolymer latexes; thermoplastic elastomers; Nylon® 66 and butadiene rubber products.

Embodiment No. 47 is the method of making a polymeric butadiene composition according to Embodiment No. 45, further comprising incorporating the polymeric butadiene composition so made into a shaped article.

Embodiment No. 48 is the method of making a polymeric butadiene composition according to Embodiment No. 46, wherein the polymeric butadiene composition is a butadiene rubber product.

Embodiment No. 49 is the method according to Embodiment No. 48, wherein the butadiene rubber product is selected from the group consisting of: emulsion styrene-butadiene rubber; solution styrene-butadiene rubber; polybutadiene rubber; nitrile rubber and polychloroprene rubber.

Embodiment No. 50 is the method of making a butadiene rubber product according to Embodiment No. 49, further comprising incorporating the butadiene rubber product so made into a shaped article.

Embodiment No. 51 is the method according to Embodiment No. 46, wherein the polymeric butadiene composition is a butadiene rubber product selected from the group consisting of: emulsion styrene-butadiene rubber; solution styrene-butadiene rubber and polybutadiene rubber.

Embodiment No. 52 is the method of making a polymeric butadiene composition according to Embodiment No. 50, further comprising incorporating the butadiene rubber product so made into a tire.

While the invention has been described in detail, modifications within the spirit and scope of the invention will be readily apparent to those of skill in the art. In view of the foregoing discussion, relevant knowledge in the art and references discussed above in connection with the Background and Description of the Invention, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method of oxidatively dehydrogenating a butene reactant to butadiene comprising:
   (a) providing a first gaseous feed stream to a first adiabatic, catalytic reaction zone at a first-stage inlet temperature, the first feed stream including said butene reactant, oxygen and superheated steam, wherein the molar ratio of superheated steam to butene reactant is less than 10 mol/mol;
   (b) oxidatively dehydrogenating said butene reactant in said first adiabatic, catalytic reaction zone to provide a first-stage effluent stream enriched in said butadiene product at a first-stage effluent temperature above said first-stage inlet temperature, by an amount referred to as a first reaction zone temperature rise;
   (c) cooling the first-stage effluent stream in a first heat transfer zone to a second-stage inlet temperature lower than said first-stage effluent temperature to provide a second gaseous feed stream comprising superheated steam, butene reactant and butadiene product, wherein the second stage inlet temperature is lower than said first stage effluent temperature by an amount referred to as a first heat transfer zone temperature reduction;
   (d) feeding said second gaseous feed stream at said second-stage inlet temperature to a second adiabatic, catalytic reaction zone along with additional oxygen and additional steam, said additional steam being added in an amount of from 0 mol/mol to 10 mol/mol of steam/butene reactant;
   (e) oxidatively dehydrogenating said butene reactant in said second adiabatic, catalytic reaction zone to provide a second stage effluent stream further enriched in said butadiene product at a second stage effluent temperature above said second-stage inlet temperature by an amount referred to as a second reaction zone temperature rise,
   wherein said first reaction zone temperature rise and said second reaction zone temperature rise are at least 200° F. (111° C.) and said first heat transfer zone temperature reduction is at least 50% of the value of the first reaction zone temperature rise, the liquid hourly space velocity (LHSV) of the butene reactant is at least 3 hr$^{-1}$, the molar yield of butadiene per pass is at least 75% and the total added steam/butene ratio is 16 or less.

2. The method according to claim 1, wherein said first reaction zone temperature rise and said second reaction zone temperature rise are at least 250° F. (139° C.).

3. The method according to claim 1, wherein said first reaction zone temperature rise and said second reaction zone temperature rise are at least 350° F. (194° C.).

4. The method according to claim 1, wherein said first reaction zone temperature rise and said second reaction zone temperature rise are from 275° F. (153° C.) to 400° F. (222° C.).

5. The method according to claim 1, wherein the first reaction zone temperature rise or the second reaction zone temperature rise are from 275° F. (153° C.) to 400° F. (222° C.).

6. The method according to claim 1, wherein said first-stage effluent temperature and said second stage effluent temperature are less than 1200° F. (667° C.).

7. The method according to claim 1, wherein said first heat transfer zone temperature reduction is at least 75% of the value of the first reaction zone temperature rise.

8. The method according to claim 1, wherein the amount of steam added to the second gaseous feed stream is from 0.5 mol/mol to 9 mol/mol of steam/dehydrogenation reactant such that the total steam added is from 8 mol/mol to 16 mol/mol of steam/dehydrogenation reactant.

9. The method according to claim 1, wherein the LHSV of the butenes is greater than 3.5.

10. The method according to claim 1, wherein the conversion of butenes is 85 mol % or greater.

11. The method according to claim 10, wherein the selectivity to butadiene is 92 mol % or greater.

12. The method according to claim 1, wherein the selectivity to butadiene is from 90 mol % to 95 mol %.

13. A method of oxidatively dehydrogenating a dehydrogenation reactant comprising:
   (a) providing a first gaseous feed stream to an inlet of a first adiabatic, catalytic reaction zone comprising a first catalyst bed of granules of oxidative dehydrogenation catalyst at a first-stage inlet temperature, the first feed stream including a dehydrogenation reactant, oxygen and superheated steam, wherein the molar ratio of superheated steam to dehydrogenation reactant is less than 10 mol/mol,
      said first catalyst bed of oxidative dehydrogenation catalyst having associated therewith a plurality of temperature sensing devices adapted to measure temperature in the first catalyst bed along a direction of flow;
   (b) oxidatively dehydrogenating dehydrogenation reactant in said first adiabatic, catalytic reaction zone to provide a first-stage effluent stream enriched in said dehydrogenated product at a first-stage effluent temperature above said first-stage inlet temperature, by an amount referred to as a first reaction zone temperature rise,
      while controlling inlet conditions to said first adiabatic reaction zone such that the oxidative dehydrogenation reaction initially occurs in the layers of said first catalyst bed most distal to said inlet of said first reaction zone, including in an active region of the first catalyst bed of said first catalytic reaction zone and monitoring the temperature along the length of the bed and from time to time, increasing the inlet temperature so that the active region of the catalyst bed of said first catalytic reaction zone migrates toward said first reaction zone inlet;
   (c) cooling the first-stage effluent stream in a first heat transfer zone to a second-stage inlet temperature lower than said first-stage effluent temperature to provide a second gaseous feed stream comprising superheated steam, dehydrogenation reactant and dehydrogenated product, wherein the second stage inlet temperature is lower than said first stage effluent temperature by an amount referred to as a first heat transfer zone temperature reduction;
   (d) feeding said second gaseous feed stream at said second-stage inlet temperature to a second adiabatic, catalytic reaction zone comprising a second catalyst bed of granules of oxidative dehydrogenation catalyst along with additional oxygen and additional steam, said additional stream being added in an amount of from 0 mol/mol to 10 mol/mol of steam/dehydrogenation reactant,
      said second catalyst bed of oxidative dehydrogenation catalyst having associated therewith a plurality of temperature sensing devices adapted to measure temperature in the first catalyst bed along a direction of flow;
   (e) oxidatively dehydrogenating dehydrogenation reactant in said second adiabatic, catalytic reaction zone to provide a second stage effluent stream further enriched in said dehydrogenated product at a second stage effluent temperature above said second-stage inlet temperature by an amount referred to as a second reaction zone temperature rise, while controlling inlet conditions to said second adiabatic reaction zone independently of controlling inlet conditions to said first adiabatic, catalytic reaction zone such that the oxidative dehydrogenation reaction initially occurs in the second adabiatic, catalytic reaction zone in the layers of said second catalyst bed most distal to said inlet of said second reaction zone, including in an active region of the second catalyst bed of said second catalytic reaction zone and monitoring the temperature along the length of the bed and from time to time, increasing the inlet temperature so that the active region of the catalyst bed of said second catalytic reaction zone migrates toward said second reaction zone inlet, wherein said first reaction zone temperature rise and said second reaction zone temperature rise are at least 200° F. (111° C.) and said first heat transfer zone temperature reduction is at least 50% of the value of the first reaction zone temperature rise.

14. The method of oxidatively dehydrogenating a dehydrogenation reactant according to claim 13, wherein the temperature sensing devices comprise thermocouples.

15. The method of oxidatively dehydrogenating a dehydrogenation reactant according to claim 13, operated continuously for at least 2400 hours.

16. A method of making a polymeric butadiene composition comprising:
  (a) oxidatively dehydrogenating a linear butene by way of:
    (i) providing a first gaseous feed stream to a first adiabatic, catalytic reaction zone at a first-stage inlet temperature, the first feed stream including said butene, oxygen and superheated steam, wherein the molar ratio of superheated steam to butene is less than 10 mol/mol;
    (ii) oxidatively dehydrogenating butene in said first adiabatic, catalytic reaction zone to provide a first-stage effluent stream enriched in butadiene at a first-stage effluent temperature above said first-stage inlet temperature, by an amount referred to as a first reaction zone temperature rise;
    (iii) cooling the first-stage effluent stream in a first heat transfer zone to a second-stage inlet temperature lower than said first-stage effluent temperature to provide a second gaseous feed stream comprising superheated steam, butene and butadiene, wherein the second stage inlet temperature is lower than said first stage effluent temperature by an amount referred to as a first heat transfer zone temperature reduction;
    (iv) feeding said second gaseous feed stream at said second-stage inlet temperature to a second adiabatic, catalytic reaction zone along with additional oxygen and additional stream, said additional steam being added in an amount of from 0 mol/mol to 10 mol/mol of steam/butene;
    (v) oxidatively dehydrogenating butene in said second adiabatic, catalytic reaction zone to provide a second stage effluent stream further enriched in butadiene at a second stage effluent temperature above said second-stage inlet temperature by an amount referred to as a second reaction zone temperature rise, wherein said first reaction zone temperature rise and said second reaction zone temperature rise are at least 200° F. (111° C.) and said first heat transfer zone temperature reduction is at least 50% of the value of the first reaction zone temperature rise, the liquid hourly space velocity (LHSV) of the butene reactant is at least 3 $hr^{-1}$, the molar yield of butadiene per pass is at least 75% and the total added steam/butene ratio is 16 or less; and
  (b) incorporating the butadiene so produced into the polymeric butadiene composition.

17. The method of making a polymeric butadiene composition according to claim 16, wherein the polymeric butadiene composition is a butadiene rubber product.

18. The method of making a polymeric butadiene rubber product according to claim 17, further comprising incorporating the butadiene rubber product so made into a tire.

* * * * *